United States Patent [19]

Powell et al.

[11] 4,264,573
[45] Apr. 28, 1981

[54] PHARMACEUTICAL FORMULATION FOR SLOW RELEASE VIA CONTROLLED SURFACE EROSION

[75] Inventors: David R. Powell; Vithal K. Patel, both of Baudette, Minn.

[73] Assignee: Rowell Laboratories, Inc., Baudette, Minn.

[21] Appl. No.: 40,789

[22] Filed: May 21, 1979

[51] Int. Cl.³ .......................... A61K 9/22; A61K 9/26
[52] U.S. Cl. ........................................ 424/19; 424/22; 424/80
[58] Field of Search ................................ 424/19–22, 424/80, 361, 362

[56] References Cited

U.S. PATENT DOCUMENTS

| | | | |
|---|---|---|---|
| 2,820,741 | 1/1958 | Endicott et al. | 424/80 |
| 2,918,411 | 2/1959 | Hill | 424/80 |
| 3,034,911 | 5/1962 | McKee et al. | 424/361 |
| 3,062,720 | 11/1962 | Costello | 424/22 |
| 3,079,303 | 2/1963 | Raff et al. | 424/35 |
| 3,102,845 | 9/1963 | Fennell | 424/22 |
| 3,145,146 | 8/1964 | Lieberman et al. | 424/80 |
| 3,148,124 | 9/1964 | Gaunt | 424/22 |
| 3,322,633 | 5/1967 | Simoons | 424/80 |
| 3,424,842 | 1/1969 | Nurnberg | 424/361 |
| 3,458,622 | 1/1969 | Hill | 424/22 |
| 3,507,952 | 4/1970 | Rednick et al. | 424/22 |
| 3,577,514 | 5/1971 | Robinson | 424/22 |
| 3,629,393 | 12/1971 | Nakamoto et al. | 424/22 |
| 3,632,778 | 1/1972 | Sheth et al. | 424/361 |
| 3,725,556 | 4/1973 | Hansson et al. | 424/361 |
| 3,773,920 | 11/1973 | Nakamoto et al. | 424/22 |
| 3,773,921 | 11/1973 | Sheth et al. | 424/22 |
| 3,950,508 | 4/1976 | Mony et al. | 424/362 |
| 3,980,766 | 9/1976 | Shaw et al. | 424/80 |
| 4,143,129 | 3/1979 | Marsden | 424/80 |

*Primary Examiner*—Shep K. Rose
*Attorney, Agent, or Firm*—Millen & White

[57] ABSTRACT

A pharmaceutical composition in tablet form for oral administration comprises:

(a) 30–90% by weight of an active ingredient having a water solubility (20° C.) of about 1/10–1/500 (w/w);
(b) 1–40% by weight of an excipient which is pharmaceutically acceptable in oral tablets and which has a water solubility (20° C.) of about 1/1–1/20 (w/w);
(c) 0–20% by weight of a binder which is pharmaceutically acceptable in oral tablets;
(d) 0–50% by weight of an excipient which is pharmaceutically acceptable in oral tablets and which has a water solubility (20° C.) of about 1/1–1/5 (w/w);
(e) 0.5–5% by weight of a die wall lubricant pharmaceutically acceptable in oral tablets;
(f) 0–5% by weight of a surface active agent pharmaceutically acceptable in oral tablets; and
(g) 0–1.0% by weight of a disintegration agent pharmaceutically acceptable in oral tablets;

whereby the active ingredient has a slow in vivo release rate due to controlled surface erosion of the tablet.

4 Claims, 2 Drawing Figures

PHARMACEUTICAL FORMULATION FOR SLOW RELEASE VIA CONTROLLED SURFACE EROSION

BACKGROUND OF THE INVENTION

Various techniques for formulating active ingredients are known in order to selectively control the resultant release rate of the drug, e.g., via sustained release, slow release, fast release, etc. Often, it is not only important to control the release rate, but also to control the shape of the release curve, i.e., the functional dependence of the in vivo concentration of the drug versus time. Simultaneous attainment of both goals is generally most difficult.

Firstly, it is important for any pharmaceutical formulation technique to provide the capability of preselecting a desired release rate which can be tailored to the unique characteristics of each drug. For example, many formulations exist which permit selection of very slow release rates, i.e., sustained release formulations. (See, e.g., U.S. Pat. No. 3,641,236 based upon glycerol fatty acid esters and U.S. Pat. No. 3,950,508 based upon alkyl celluloses and inert powders such as talc, which, in combination with other ingredients, produce a gradual disaggregation of the sustained release tablet.) These can often cause toxicity and other side effects due to an inordinately long presence of the drug in the body. Thus, methods of preselecting somewhat faster release rates, i.e., slow release rates—midway between fast and sustained rates—are needed.

Moreover, many formulations result in a release curve having a high concentration peak at the beginning of release which subsequently tails off at longer times (see, e.g., curve (----) of FIG. 1). Such concentration peaks are generally undesirable since they can lead to toxicity and/or other adverse side effects. Additionally, their existence significantly limits the freedom to increase the unit dosage of administration. Such an increased dosage would correspondingly increase the peak concentration. Under such circumstances, it is not possible to decrease the frequency of administration by increasing the unit dosage. This is a significant disadvantage since it is well established that the likelihood that a patient will fail to take doses of his medication is directly proportional to the required frequency of administration.

As can be seen, in very many instances, it is most desirable to achieve both a relatively slow release rate of medication and a minimal peak concentration. These should further be selectable so that the resultant in vivo absorption is desirably controlled and the bioavailability of the drug is maximized.

SUMMARY OF THE INVENTION

Accordingly, it is an object of this invention to provide a slow release pharmaceutical formulation which provides the capability of decreasing the peak concentration of the released active ingredient.

It is another object of this invention to provide such a pharmaceutical formulation by which the release rate and release curve shape can be controlled in order to maximize in vivo bioavailability of the active ingredient.

It is a further object of this invention to provide such a formulation which can be so controlled in order to simultaneously minimize adverse side effects of the released active ingredient.

Upon further study of the specification and appended claims, further objects and advantages of this invention will become apparent to those skilled in the art.

These objects have been attained by providing a pharmaceutical composition in tablet form for oral administration comprising:

(a) 30–90% by weight of an active ingredient having a water solubility (20° C.) of about 1/10—1/500 (w/w);

(b) 1–40% by weight of an excipient which is pharmaceutically acceptable in oral tablets and which has a water solubility (20° C.) of about 1/1–1/20 (w/w);

(c) 0–20% by weight of a binder which is pharmaceutically acceptable in oral tablets;

(d) 0–50% by weight of an excipient which is pharmaceutically acceptable in oral tablets and which has a water solubility (20° C.) of about 1/1–1/5 (w/w);

(e) 0.5–5% by weight of a die wall lubricant pharmaceutically acceptable in oral tablets;

(f) 0–5% by weight of a surface active agent pharmaceutically acceptable in oral tablets; and (g) 0–1.0% by weight of a disintegration agent pharmaceutically acceptable in oral tablets;

whereby the active ingredient has a slow in vivo release rate due to controlled surface erosion of the tablet.

Optionally, this pharmaceutical composition may also contain, in place of a corresponding amount of active ingredient (a), 0–90% by weight of an inert bulking excipient pharmaceutically acceptable in oral tablets, which has a water solubility (20° C.) of about 1/10–1/500 (w/w).

In another aspect, this invention provides a method of administering an active ingredient with a slow release rate and a minimal peak in vivo concentration which comprises administering the above described pharmaceutical composition.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

Figure 1:
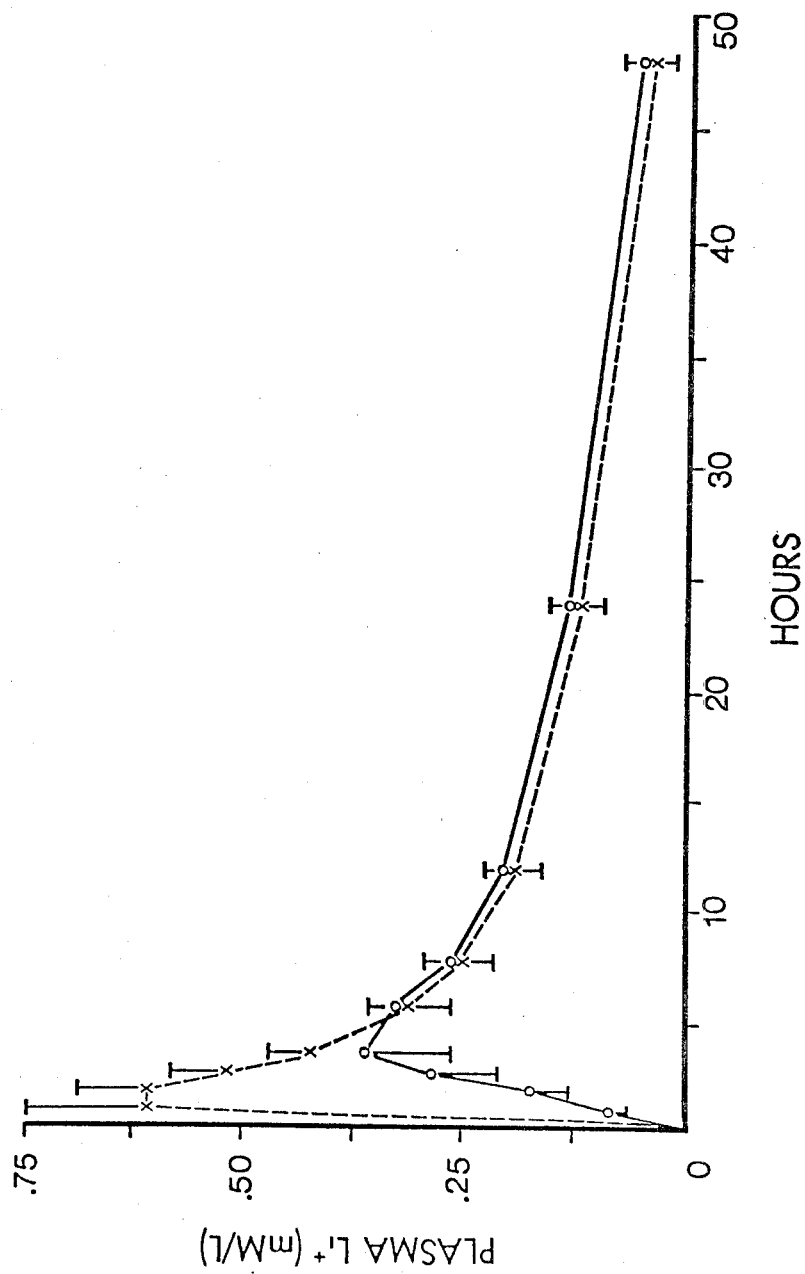
FIG. 1 shows the in vivo plasma concentrations (mean curve±S.D.) achieved as a function of time upon a single oral dose (12 human subjects-crossover design) of the standard fast release Li formulation x----x, and of the slow release formulation o—o of this invention.

The mechanism by which the active ingredient is released from the pharmaceutical composition of this invention can be best described as controlled surface erosion. This means that the tablet becomes uniformly smaller and smaller as it erodes and dissolves. Tests have shown that tablet cores retain their identity through at least 90% of the dissolution process and that the dissolution rate is a surface controlled phenomenon.

These dissolution rates fall within the realm of slow release rates as conventionally defined. That is, via the pharmaceutical formulations of this invention, the drug is yielded to the blood system at a significantly slower rate than typical fast release (disintegration) dosage forms while maintaining a rate significantly faster than conventional sustained release products. Thus, the inventive pharmaceutical compositions produce rates which are in the intermediate range. Without intending to limit the scope of this invention in any way, typical slow release dissolution rates may be quantified as those which permit about 0.25-1.0% of the active ingredient to be released and dissolved per minute as measured by the U.S.P. basket method (XIX U.S.P. 651, the basket being rotated at 150 rpm).

Furthermore, since the release rate of the inventive pharmaceutical formulation is a surface-controlled phenomenon, in general, zero order release rates are obtained. That is, the amount of drug in solution at any time can be predicted from the weight of the undissolved tablet. In tests, it has been shown that at least 98% of the total content of the active ingredient can be accounted for in accordance with their theory. (The amount of drug not accounted for was assumed to reside in undissolved granules or particles which had eroded from the tablet but had not yet dissolved.) Thus, the in vitro dissolution rate in general will obey the following relationship:

$$C_t = C_o - Kt$$

wherein
$C_0$ is the initial amount of drug in the tablet;
$C_t$ is the amount of drug remaining undissolved, at time (t);
K is the zero-order rate constant; and
t is the time.

Tests have also shown that $C_t$ may be approximated by simply determining the weight of the dry core which remains at any given time as follows:

$$C_t \cong C_{ta} = C_o W_t / W_o$$

wherein
$C_{ta}$ is the approximated value;
$W_t$ is the core weight remaining at time t; and
$W_o$ is the initial weight of the tablet.

Since these formulae fit the observed data well (e.g., see the Examples), it can be seen that the release of the drug with subsequent rapid dissolution is a surface-controlled phenomenon and that release and dissolution obey a zero-order rate equation, i.e., the dissolution rate is independent of the concentration dissolved.

The desirability of such zero order dissolution rates is well recognized; see, e.g., U.S. Pat. No. 3,965,255, The New England Journal of Medicine, 299:16, (852-857) 1978.

The exact nature of the surface dissolution is, of course, a function of the overall physical effects due to the combination of all ingredients, including the active ingredient in the pharmaceutical formulation. These physical effects relate to the ultimate wettability, penetrability, cohesion and erosion of the resultant tablet and, in essence, govern the ultimate dissolving rate. Each ingredient generally has a major effect on one tablet property, but may also play secondary and tertiary roles.

One of the principal characteristics of the ingredients required in the pharmaceutical composition of this invention is that they are essentially of a water soluble nature and do not include gums, pH-dependent excipients, waxes, fats or the general type of polymers generally associated with sustained release products. The only polymer employed in generally that for the binder. Additionally, the release effects are attained without the need for layers, beads or enteric materials within the product. As a result, the tablet is manufactured by conventional techniques using standard equipment.

The above described amounts and solubilities for each of the ingredients are tailored in view of each other so that the desired slow release, low peak concentration effects will be obtained. It is possible that one or more of these solubility and/or percent content ranges may be varied somewhat so that the resultant new combination will still produce the desired release characteristics. Moreover, it can be seen from the following description, there is some overlap among the classes of ingredients as defined. This is fully acceptable as long as the final formulation meets the prescribed numerical characteristics. This described formulation provides the necessary latitude for achieving a particularly desired slow release rate and attendant low peak concentration by balancing the solubility retarding effects of the more insoluble ingredients such as the drug with the solubility enhancing effects of the more soluble ingredients such as the erosion controller, whereby the ratio of all ingredients is adjusted to produce the precise desired slow dissolution rate (slow absorption rate).

Suitable drugs (a) include any for which there exists a specific reason for minimizing peak serum levels via the controlled surface erosion phenemenon of this invention. For example, such drugs include antibiotics, cardiovascular agents, analgesics, antipyretics, antiinfectives, antacids, gastrointestinal medications, steroids, CNS stimulants, psychopharmacologic drugs, antineoplastic and immunosuppressive drugs, antihistamics, vitamins, essential minerals, sympathomimetic and parasympathomimetic drugs, antitussives, diuretics, sedatives, hypnotics, antiepileptics, decongestants, antiasthmatics, etc.

By formulating such drugs in accordance with this invention, deleterious high rates of absorption and/or peak blood levels, associated with toxic and/or adverse side effects, can be avoided. Simultaneously, because of the reduced absorption rates and the blunting of the serum peak concentration via the controlled surface erosion of this invention, it is simultaneously possible to increase the unit dosage of the drug and to correspondingly reduce its frequency of administration.

In general, the amount of the active ingredient will be 30-90% by weight of the tablet. The drug should have a solubility in water (20° C.) of about 1 weight part in 10 weight parts to 1 weight part in 500 weight parts. In general, the half-life of the drug will not be critical since the formulation does not produce sustained release but rather slow controlled release.

In addition to its role as a medicament, the active ingredient also affects the nature of the release rate which is obtained, primarily by contributing towards penetration control and cohesion. These factors are considered in the definition of the foregoing weight percent range and solubility range.

Ingredient (b) functions primarily as a surface uniformity control agent during dissolution and erosion. The selection of a particular agent is not especially critical as long as it is a conventional pharmaceutically acceptable excipient which is water soluble and compatible with oral tablet manufacturing. Preferably, the agent should have a water solubility (20° C.) of about 1 weight part in 1 weight part to 1 weight part in 20 weight parts. It is usually employed in the composition in amounts of 1–40% by weight of the final tablet.

Suitable such pharmaceutical excipients include inorganic compounds such as the chloride, sulfate and phosphate salts of potassium, sodium and magnesium as well as the calcium citrate, phosphate, lactate, gluconate and succinate salts. Suitable organic compounds for use as the surface uniformity control agent include the pharmaceutically acceptable and conventional mono-saccharides and di-saccharides, for example, glucose, fructose, xylose, galactose, sucrose, maltose, mannitol and xylitol.

Ingredient (c) of the pharmaceutical composition is a fully conventional pharmaceutically acceptable binder for oral tablets which is normally employed for the purpose of aiding in the formation of granules during the granulation steps, or for modifying the compression characteristics during the compression steps, or for aiding during other conventional tablet forming processes. As mentioned, the slow release composition of this invention does not require the presence of such conventional binders as gums, waxes, relatively insoluble polymers, etc. which are always required in sustained release compositions and many other slow release compositions. However, of course, such ingredients can be employed where desirable for other reasons. Suitable such fully conventional binders include povidone (polyvinylpyrrolidone), polyvinylalcohol, polyethyleneglycol, sucrose, lactose, gelatin, starch paste, acacia, tragacanth, etc.

In general, the binders are included in the inventive pharmaceutical composition in amounts of 0–20% by weight of the final tablet. They may not always be needed since some compositions of this invention will be inherently compressable and/or granulatable, e.g., by the slugging technique or by the addition of a subsequently evaporatable, activating solvent such as water, alcohol, acetone, etc. In addition to the primary binding cohesion control effect of this ingredient, wettability control and penetration control will also often be affected by its inclusion depending, of course, on the specific characteristics of the particular binder employed.

Ingredient (d) generally serves as the primary erosion rate controlling agent. Consequently, this ingredient generally has a high water solubility, e.g., 1 weight part in 1 weight part to 1 weight part in 5 weight parts.

Suitable such agents include the polyhydric alcohols, which in general also should be suitable for dry mixing with the active granulations or powders. For example, such agents include sorbitol, lactose, sucrose mannitol, dextrose, fructose, xylitol, etc. The amount of this ingredient is selected in accordance with the desired rate of dissolution erosion and generally is in the range of 0–50% based on the weight of the final tablet.

Ingredient (e) is a fully conventional pharmaceutically acceptable die wall lubricant for inclusion in oral tablets. This ingredient is required in order to facilitate the ejection of the tablet from the die after the compression step by lubrication of the tableting tool. Suitable such conventional die wall lubricants include the stearate salts such as calcium, magnesium, and zinc, as well as stearic acid, mineral oil, vegetable oil derivatives, polyethylene glycols and talc.

In general, 0.5–5% by weight of the final tablet of this ingredient is included.

Ingredient (f) is a surface active agent which is also pharmaceutically acceptable and fully conventional for use in oral tablets. This ingredient provides wettability for the purpose of controlling medium penetration and surface erosion. Suitable such conventional surface active agents include sodium lauryl sulfate, magnesium lauryl sulfate, DDS (dioctyl sodium sulfosuccinate), triethanolamine, polyoxyethylene sorbitan and poloxalkol derivatives, with a hydrophil-lipophil balance (HLB) above 12, and quaternary ammonium salts. Surface active agents are generally included in the composition in amounts of 0–5% by weight of the final tablet.

Ingredients (e) and (f) may also be added to the composition in conventionally combined form. Such combinations are commercially available and are provided as a homogeneous mixture of the two ingredients prepared by spray drying or other techniques. Such commercially available combined lubricants and surface active systems include Stear-o-wet C and Stear-o-wet M.

Ingredients (g) of the inventive compositions are fully conventional disintegrating agents employed in pharmaceutical oral tablets. These also serve as stabilizers and penetration control agents to some degree. Their stabilizing effects relate to the stability of the achieved release rates over long periods of storage, e.g., their zero order nature is retained over long time periods on the order of years. Such conventional components include starch and starch derivatives, wood and cotton cellulose derivatives of the microcrystalline or cross linked types or other polymeric materials which are conventionally employed to maintain active tablet surfaces and absorb moisture, causing swelling. The ingredients are employed in low concentrations, e.g., 0–1%. It is also possible to employ larger amounts when it is desired to speed up the erosion process where necessary.

Very often, an active ingredient is generally dosed in high concentrations. Typical such high dosage drugs include lithium, theophylline, guinidine sulfate, etc. Such drugs are dispensed in unit dosages from 50–500 mg, for example. Such dosages are quite readily compatible with the pharmaceutical composition of this invention as defined above. However, it is often desired to formulate such drugs in dosage ranges of less than 50 mg, e.g., 1–<50 mg per tablet. In such situations, ingredient (h) can be incorporated into the tablet replacing a corresponding amount of the active ingredient per se. In this way, slow release base formulations for the more potent type of drugs can be prepared at low dosages.

Since excipients (h) are used to replace active ingredient (a), they should have the same solubility properties, e.g., water solubilities (20° C.) of about 1 weight part in 10 weight parts to 1 weight part in 500 weight parts. The amount of this innocuous bulking excipient, i.e., filler, is to be chosen depending upon the desired dosage of the active ingredient as well as on the other factors discussed above with respect to the active ingredient per se, e.g., its effect on the surface erosion control mechanism. Generally, the amount of ingredient (h) is 0–90% by weight of the finally produced tablet, for example, less than 30–less than 90% by weight. Usually, at least 1–10% by weight will be present.

Such innocuous bulking excipients (fillers) are fully conventional and include the pharmaceutically acceptable excipients for oral tablets such as inorganic salts, both mineral and mineral organic, carbohydrates, proteins, emulsifiable fats and the like. Specific examples include calcium salts, such as the lactate, gluconate, glycerylphosphate, citrate, phosphate monobasic and dibasic, succinate, sulfate and tartrate, as well as the same salts of aluminum and magnesium. Typical such carbohydrates include the conventional mono- and disaccharides as well as other suitable polyhydric alcohols.

The specific proportions of all ingredients for a particular active ingredient will be determined by the release rate characteristics desired, in accordance with routine pharmaceutical testing procedures. For example, the release rate can be increased by generally increasing the amounts of ingredients which have a high water solubility or which increase the erosion rate, e.g., ingredient (d), the erosion rate controller, ingredient (g), the disintegrating agent, etc.

The methods used in combining all ingredients into the final tablet should be practiced in accordance with conventional pharmaceutical considerations. For example, conventional practices ensuring lot-to-lot reproducibility should be employed. For example, as is conventional, the particle size of ingredients such as the drug, the salts such as sodium chloride and the erosion control ingredients such as sorbitol should be maintained as consistent as possible. In general, the drug and the excipients should be incorporated into the compositions in a particle size selected below 60 mesh, e.g., 60-200 mesh in order to ensure proper mixability and homogeneity. This operation may be carried out by screening or milling through a pharmaceutically compatible machine with subsequent blending.

The various blending, mixing and tableting steps should also be maintained as consistent as possible since the conditions employed can often have an impact on the release rate of the finally produced tablet. Consequently, once the manufacturing details compatible with a given pharmaceutical composition in order to achieve a desired release rate are determined, they should be followed as strictly as possible.

A typical sequence of operations is as follows: first, the drug is thoroughly blended with the ingredient selected to maintain the surface uniformity during erosion. It is then granulated with the appropriate binder/solvent system in order to produce granules. The amount of solvent (e.g., water) employed during the wet granulation step will, of course, have an impact on the resultant bulk density in the final granulation. Typically, such granulation tapped bulk densities will be within the range of 0.5 g/ml-1.5 g/ml. The formed dried granules are then conventionally sized in order to provide an appropriate particle size distribution, e.g., between 20 and 100 mesh with not more than 70% classified as fines, i.e., passing through 100 mesh openings.

The finished granulate is then blended with the erosion controlling agent, the stabilizer (disintegrating agent), the die wall lubricant and the surface active agent in a suitable mixer. The final mixture is compressed into tablets of suitable and consistent hardness, e.g., 5-20 kg. The compressed tablet may be conventionally coated for esthetic purposes if desired.

As is also fully conventional, the in vitro determined dissolution rates and other characteristics are subsequently correlated with in vivo absorption and blood levels. This correlation is also used in quality control in order to ensure batch-to-batch uniformity.

As a general guideline for utilization of the mechanisms and principles of controlled surface erosion, one skilled in the science may combine candidate drugs with an acceptable agent useful for controlling surface uniformity as described. This homogenous mixture is then converted to a base or foundation granulation as described. Sub-formulations are prepared using various amounts of a primary erosion rate controlling agent. Tablets prepared from these several sub-formulations will determine by in vitro dissolution testing which one(s) are likely to yield the proper in vivo absorption rate as desired for the candidate drug. In vivo studies are then conducted to determine that the proper dissolution and absorption rates have been achieved.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of lithium carbonate slow release tablets
Desired characteristics:

The conventional lithium formulation is a fast release product. It was desired to reduce the side effects attendant to the administration of such conventional tablets and to reduce the frequency of dosing from the normal 3-4 times a day to 1-2 times a day. Additionally, it was desired to prepare a formulation providing gradual and complete release of lithium ion into the bloodstream, i.e., providing a slow release rate of the active lithium ion. Sustained release mechanisms are not only undesirable since excessively retarded release rates cause diarrhea due to the presence of lithium ion in the lower bowel, but also because the half-life of absorbed lithium is not compatible with sustained release formulations. In addition, it was desired to achieve a release rate which would guarantee complete bioavailability of the lithium ion. It was also highly desirable that the release rate follow zero-order kinetics.

Very importantly, it was further desired that the initially high concentration peak of absorbed lithium ion in the blood serum be reduced as significantly as possible, thereby avoiding the adverse side reactions associated therewith and enabling the employment of higher dosages at less frequent intervals.

Additionally, it was preferred that the new lithium dosage form be highly reproducible from batch to batch and be formulatable using only conventional techniques and standard equipment. Lithium, of course, is a well known antidepressant and is often used in the treatment of the manic depressive patient.

New lithium tablet formulated per this invention

It was found that by employing the pharmaceutical composition of this invention, all of these ends could be simultaneously achieved. The tablets are prepared as follows.

Sodium chloride is milled through a Whistler Mill using a small slotted screen. 8,000 grams of this sodium chloride and 60,000 grams of lithium carbonate are charged into a 5 cubic feet Ribbon Blender and blending is carried out for 5 minutes. The blender is discharged and the powder mixture is passed through a Fitzmill at a high speed (hammers). The powder is then returned to the blender and wet granulated (16,000 grams of water) with povidone. The binder solution in water is added while the mixer is running. The resultant wet mass is passed through the Fitzmill (¼ inch, perforated band, hammers forward) at high speed. The resultant mass is trayed and dried overnight (16 hours at 55° C.). The dried mixture is sized through the Fitzmill (2A with knives at medium speed). The resultant blend is returned to the Ribbon Blender. Sorbitol powder is passed through a 40-mesh screen along with Stearowet C (a combination of calcium stearate and sodium lauryl sulfate). 2,000 grams of the Stearowet C and 8,000 grams of the sorbitol powder are added to the blender along with 200 grams of sodium starch glycolate and the blend is mixed for 5 minutes. The resultant mixture is compressed into 200,000 tablets using a ⅜″ standard concave tooling, uppers plain, lowers plain.

Each tablet weighs 406 mg and has the following composition: lithium carbonate, 300 mg; sodium chloride, 40 mg; polyvinyl pyrrolidone 15 mg; Stearowet C, 10 mg; sorbitol, 40 mg; and sodium starch glycolate, 1 mg. The compressed tablets have a hardness of 8–10 kg, a friability of NMR 0.4% and a thickness of 0.175 inches.

These weight contents correspond to ingredient contents of (a) 73.89, (b) 9.85, (c) 3.70, (d) 9.85, (e) and (f) 2.46, and (g) 0.25. Considering the composition of Stearowet C, the respective contents of (e) and (f) are 2.31% and 0.15%, i.e., 9.4 mg and 0.6 mg. In general, these percentages may vary within the following limits: (a) 70–80%; (b) 5–15%; (c) 2–7%; (d) 5–15%; (e) 0.9–3.3%; (f) 0.1–0.2%; and (g) 0.15–0.35%.

The 200,000 tablets produced can then be optionally coated using conventional procedures. The tablets are placed in Accela-Cota and 10,000 milliliters of a conventional clear film seal solution are sprayed thereon. Subsequently, 30,000 milliliters of a colored film seal (e.g., 1300 grams of Opaspray K-1-1243 in 30,000 milliliters of a clear film seal solution) are sprayed. This is followed by spraying of 10,000 ml of half-strength film and color solution (e.g., 215 grams of the same ingredient in 10,000 ml of half-strength film seal solution). The spraying is finished with 5,000 ml of half-strength film seal solution. The coated tablets are dried in a pan for one hour using 800–1,000 cfm of air at 30°–35° C. They are trayed and dried at 20°–23° C. overnight. After submission of, e.g., 150 tablets to quality control for approval, the tablets are polished in a pan with 2 grams of Carnauba Wax. They are then optionally imprinted and subjected to normal control laboratory procedures for testing, followed by conventional inspection.

EXAMPLE 2

Dissolution properties

Tablets prepared in several runs using the procedures of Example 1 were tested for their dissolution properties as a function of storage time at 20°–22° C. The results are summarized in the Table below:

| STABILITY STORAGE 20–22° C. | | | | |
|---|---|---|---|---|
| Storage Period | $T_{100\%}$ | K | n | r |
| Run Number 1 | | | | |
| Initial | 106.7 | 2.94 | 9 | 0.9798 |
| 10 mos. | 110.3 | 2.89 | 24 | 0.9956 |
| 21 mos. | 103.2 | 3.03 | 24 | 0.9859 |
| Run Number 2 | | | | |
| Initial | 100.8 | 3.14 | 12 | 0.9864 |
| 3 mos. | 104.5 | 3.01 | 24 | 0.9935 |
| 6 mos. | 98.7 | 3.23 | 24 | 0.9984 |
| 18 mos. | 98.0 | 3.24 | 24 | 0.9960 |
| 24 mos. | 100.7 | 3.19 | 24 | 0.9991 |
| 36 mos. | 95.3 | 3.27 | 24 | 0.9847 |
| Run Number 3 | | | | |
| Initial | 93.6 | 3.45 | 24 | 0.9930 |
| 3 mos. | 94.8 | 3.43 | 24 | 0.9925 |
| 6 mos. | 91.5 | 3.65 | 24 | 0.9992 |
| 12 mos. | 90.7 | 3.66 | 24 | 0.9973 |
| 24 mos. | 90.3 | 3.66 | 24 | 0.9968 |
| Run Number 4 | | | | |
| Initial | 106.0 | 2.95 | 24 | 0.9977 |
| 6 mos. | 105.2 | 2.94 | 24 | 0.9967 |
| 12 mos. | 106.0 | 3.12 | 24 | 0.9975 |
| Run Number 5 | | | | |
| Initial | 97.9 | 3.21 | 24 | 0.9954 |
| 12 mos. | 93.5 | 3.32 | 24 | 0.9975 |
| Statistical Summary | | | | |
| n = 19 | 19 | 19 | | 19 |
| $\Sigma x$ = 1887.7 | | 61.33 | | 18.883 |
| $\bar{X}$ = 99.35 | | 3.23 | | 0.9938 |
| S = 6.09 | | 0.25 | | 0.0055 |
| RSD = 6.13% | | 7.74% | | 0.55% | where:
$T_{100}$ = Minutes for 100% dissolution
K = Dissolution rate mg/min.
r = Linear correlation coefficient The data demonstrate several of the superior properties of the tablets. The lot-to-lot reproducibility with regard to dissolution rate (K) is excellent, a property which is often difficult to achieve in sustained- or slow-release mechanisms in other types of tablets. The initial values for K for all runs range from 2.94 mg/min. to 3.45 mg/min. The composite statistical data for all measurements show that K has a value of 3.23±0.25 mg/min.

As indicated by the linear correlation coefficient (r), all lots at all stability intervals very closely approximate a perfect zero-order dissolution rate. This demonstrates that the controlled surface erosion phenomenon governs the dissolution of the tablet, as desired.

Of course, the data also clearly demonstrate the high storage stability of the tablets for long periods of time up to 3 years.

EXAMPLE 3

Pharmacokinetic properties of the formulations

Tablets prepared in accordance with Example 1 have been subjected to extensive clinical testing. The resultant data is summarized in Am. J. Psychiatry 135:8, 917–922 (1978), whose disclosure is entirely incorporated by reference herein.

These detailed studies confirmed that the major objectives of the formulation of Example 1 were attained. The in vivo dissolution and absorption of lithium carbonate was controlled as desired in order to reduce serum accumulation rate, reduce maximum serum concentration and permit less frequent dosing. In addition, it was determined that the active ingredient was completely bioavailable without any attendant severe side effects such as diarrhea. Advantageously, the product could be used interchangeably with the conventional fast release formulation except for less frequent administration and more desirable absorption rates. The absorption characteristics of a single oral dosage for both the standard formulation and the slow release formulation of Example 1 may be seen by inspection of FIG. 1. A plot of the first four data points of the FIG. 1 curve for the latter is shown in FIG. 2. (o----o) The linear plot demonstrates the in vivo zero-order uptake of the active ingredient. Comparison of the slope of this line with that of the normal fast release formulation (x----x in FIG. 2) illustrates the significantly slower release rate, i.e., absorption rate, achieved.

EXAMPLE 4

Slow release formulation for theophylline

Like lithium carbonate, theophylline is an active ingredient of low to moderate solubility. Several preparations of this drug having controlled release are commercially available; however, many of these products are reported to give erratic and incomplete absorption; see, e.g., New England Journal of Medicine, 299:16, (852–857), 1978.

In the absence of side effects such as lower bowel disturbances, the formulation of this drug was set for slower dissolution/erosion than for lithium carbonate in Example 1. Consequently, tablets were prepared following scaled down procedures of Example 1, containing 300 mg/tablet of theophylline and the same proportions of the other ingredients except that the amounts of sodium chloride, Povidone and sorbitol powder were reduced to 37.5%, 67% and 50%, respectively, of the amount used in Example 1, and sodium starch glycolate was omitted.

In vitro data have demonstrated that the controlled surface erosion phenomenon is the mechanism for release of theophylline from these tables. That is, the statistical data demonstrate that a zero-order release rate is involved. However, since the amounts of sodium chloride, Povidone and sorbitol are reduced, the rate of dissolution was cut by ⅓. In other words, theophylline dissolved at about 2 mg/min. whereas the product of Example 1 dissolved at about 3 mg/min. Again, dissolution variation among tablets at any sampling interval was very low. The relative standard deviations ranged from ±6.5% at 30 minutes to ±3.1% at 180 minutes when dissolution was essentially completed.

Theophylline is well known as a diuretic, cardiac stimulant and smooth muscle relaxant.

EXAMPLE 5

Slow Release Formulation for Quinidine

The solubility of Quinidine Sulfate in water is reported to be 1 part in 90; thus, this drug is yet another example for the application of the CSE (Controlled Surface Erosion) principle.

The principles and mechanisms described in this disclosure were utilized in the development of a slow release quinidine sulfate dosage form. Including the collection of in vitro dissolution data, the entire development required about 25 man-hours.

The composition was altered with regards to the agent used for controlling surface uniformity and the agent used for the primary control of erosion rate. Substitution of calcium phosphate monobasic and lactose demonstrate the formulation flexibility in the controlled surface erosion principle. Other excipients were the same as those used in examples 1 and 4.

Again, in vitro dissolution analysis showed that release followed the zero-order rate process since the linear correlation coefficient (r) was 0.9947. Dissolution rate was found to be 0.25%/min. or 0.76 mg/min. from the 300 mg quinidine sulfate tablets. Simple adjustment in the ratios of the calcium phosphate monobasic and the lactose could be made to increase or decrease erosion and dissolution rate depending on in vivo performance.

The following table summarizes controlled surface erosion examples 1, 4 and 5 with regard to the composition and concentration flexibility.

| Ingredient Category | Composition: Concentration (% w/w) | | | | | |
|---|---|---|---|---|---|---|
| | Example 1 | | Example 4 | | Example 5 | |
| | Composition | % | Composition | % | Composition | % |
| (a) | Lithium Carbonate | 73.89 | Theophylline | 84.50 | Quinidine Sulfate | 60.20 |
| (b) | Sodium Chloride | 9.85 | Sodium Chloride | 4.22 | Calcium Phosphate Monobasic | 30.10 |
| (c) | Povidone | 3.70 | Povidone | 2.82 | Povidone | 1.50 |
| (d) | Sorbitol | 9.85 | Sorbitol | 5.63 | Lactose | 5.00 |
| (e) | Calcium Stearate | 2.31 | Calcium Stearate | 2.65 | Calcium Stearate | 2.58 |
| (f) | Sodium Lauryl Sulfate | 0.15 | Sodium Lauryl Sulfate | 0.17 | Sodium Lauryl Sulfate | 0.17 |
| (g) | Sodium Starch Glycolate | 0.25 | Sodium Starch Glycolate | 0 | Sodium Starch Glycolate | 0.40 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

Figure 2:
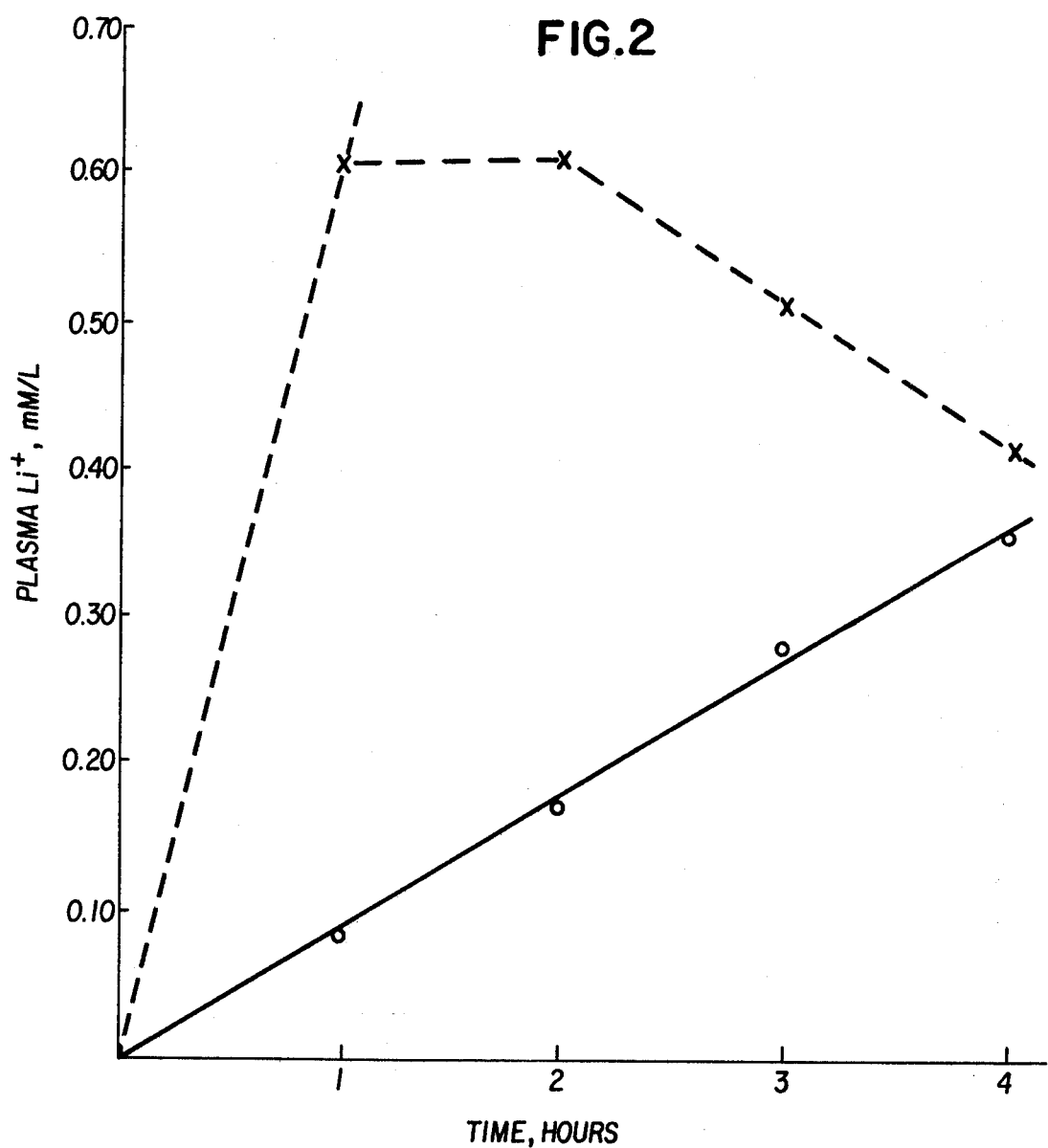
FIG. 2 shows the in vivo absorption rates (single oral dose, mean curve) for the standard fast release (x----x) Li formulation and the slow release formulation of this invention.

What is claimed is:

1. A pharmaceutical composition in tablet form for oral administration consisting essentially of
   (a) 70–80 wt.% of lithium carbonate;
   (b) 5–15 wt.% of an excipient which is pharmaceutically acceptable in oral tablets and which has a water solubility (20° C.) of about 1/1–1/20 (w/w);
   (c) 2–7 wt.% of a binder which is pharmaceutically acceptable in oral tablets;
   (d) 5–15 wt.% of an excipient which is pharmaceutically acceptable in oral tablets and which has a water solubility (20° C.) of about 1/1–1/5 (w/w);
   (e) 0.9–3.3 wt.% of a dye wall lubricant pharmaceutically acceptable in oral tablets;
   (f) 0.1–0.2 wt% of a surface active agent pharmaceutically acceptable in oral tablets; and
   (g) 0.15–0.35 wt.% of a disintegration agent pharmaceutically acceptable in oral tablets;

whereby the active ingredient has a slow zero order in vivo release rate and a plasma concentration/time curve of substantially the same shape as that of FIG. 1, due to controlled surface erosion of the tablet.

2. The pharmaceutical composition of claim 1 consisting essentially of: 70–80 wt.% of lithium carbonate; 5–15 wt.% of sodium chloride; 2–7 wt.% of polyvinylpyrrolidone; 5–15 wt.% of sorbitol; 0.9–3.3 wt.% of calcium stearate; 0.1–0.2 wt.% of sodium lauryl sulfate; and 0.15–0.35 wt.% of sodium starch glycolate.

3. The pharmaceutical composition of claim 2 consisting essentially of the following approximate amounts of ingredients: 300 mg of lithium carbonate; 40 mg of sodium chloride; 15 mg of polyvinylpyrrolidone; 9.4 mg of calcium stearate; 0.6 mg of sodium lauryl sulfate; 40 mg of sorbitol; and 1 mg of sodium starch glycolate.

4. The pharmaceutical composition of claim 1, 2 or 3 which is in the form of a tablet of a hardness of 5–20 kg.

* * * * *